US008007535B2

(12) United States Patent
Hudgins et al.

(10) Patent No.: US 8,007,535 B2
(45) Date of Patent: Aug. 30, 2011

(54) INTERBODY FUSION RING AND METHOD OF USING THE SAME

(75) Inventors: Robert Garryl Hudgins, Burnsville, MN (US); Melanie Chapman, Watsontown, PA (US); Guido Casutt, Sulz-Rickenbach (CH); Rosemary Thompson, Winterthur (CH); Thomas O. Viker, Arden Hills, MN (US); Hugh D. Hestad, Edina, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 592 days.

(21) Appl. No.: 11/421,571

(22) Filed: Jun. 1, 2006

(65) Prior Publication Data

US 2006/0293749 A1     Dec. 28, 2006

Related U.S. Application Data

(60) Provisional application No. 60/686,740, filed on Jun. 2, 2005.

(51) Int. Cl.
*A61F 2/44* (2006.01)
(52) U.S. Cl. .................................................. 623/17.12
(58) Field of Classification Search ..... 623/17.11–17.15
See application file for complete search history.

(56) References Cited

U.S. PATENT DOCUMENTS

| | | | |
|---|---|---|---|
| 3,756,389 A * | 9/1973 | Firth | 206/219 |
| 3,867,728 A * | 2/1975 | Stubstad et al. | 623/17.16 |
| 4,401,112 A | 8/1983 | Rezaian | |
| 4,501,269 A | 2/1985 | Bagby | |
| 4,759,769 A | 7/1988 | Hedman et al. | |
| 4,772,287 A | 9/1988 | Ray et al. | |
| 4,820,305 A | 4/1989 | Harms et al. | |
| 4,834,757 A | 5/1989 | Brantigan | |
| 4,904,260 A * | 2/1990 | Ray et al. | 623/17.12 |
| 4,936,848 A | 6/1990 | Bagby | |
| 4,946,458 A | 8/1990 | Harms et al. | |
| 5,015,247 A | 5/1991 | Michelson | |
| 5,015,255 A | 5/1991 | Kuslich | |
| 5,059,193 A | 10/1991 | Kuslich | |

(Continued)

FOREIGN PATENT DOCUMENTS

DE    20 2004 009 786 U1    2/2003

(Continued)

OTHER PUBLICATIONS

European Patent Office, International Search Report and Written Opinion for PCT/US2006/021342, Nov. 6, 2006, 15 pp.

*Primary Examiner* — Thomas C Barrett
*Assistant Examiner* — David W Bates
(74) *Attorney, Agent, or Firm* — Seager Tufte & Wickhem LLC

(57) ABSTRACT

The present invention provides an injectable annular ring useful in treating a deteriorating spinal disc. When used, the annular ring may be collapsed or folded in order for it to be placed through a small opening in a prepared intervertebral space within the annulus using minimally invasive techniques. Deployment or unfolding the ring in the intervertebral space provides an interior cavity bordered by the ring that is in direct contact with the vertebral endplates. When an internal volume of the ring is inject or filled with a load-bearing, hardenable material, the filled ring maintains the intervertebral spacing and prevents the ring from being expelled from the interior cavity through the small annular opening.

37 Claims, 14 Drawing Sheets

U.S. PATENT DOCUMENTS

| | | |
|---|---|---|
| 5,192,326 A | 3/1993 | Bao et al. |
| 5,263,953 A | 11/1993 | Bagby |
| 5,405,391 A | 4/1995 | Hednerson et al. |
| 5,489,307 A | 2/1996 | Kuslich et al. |
| 5,489,308 A | 2/1996 | Kuslich et al. |
| 5,514,180 A | 5/1996 | Heggeness et al. |
| 5,549,679 A | 8/1996 | Kuslich |
| 5,571,189 A | 11/1996 | Kuslich |
| 5,591,235 A | 1/1997 | Kuslich |
| 5,669,909 A | 9/1997 | Zdeblick et al. |
| 5,700,291 A | 12/1997 | Kuslich et al. |
| 5,709,683 A | 1/1998 | Bagby |
| 5,720,748 A | 2/1998 | Kuslich et al. |
| 5,735,899 A | 4/1998 | Schwartz et al. |
| 5,895,427 A | 4/1999 | Kuslich et al. |
| 5,972,031 A | 10/1999 | Biedermann et al. |
| 6,010,502 A | 1/2000 | Bagby |
| 6,015,436 A | 1/2000 | Schönhöffer |
| 6,039,763 A | 3/2000 | Shelokov |
| 6,332,894 B1 | 12/2001 | Stalcup et al. |
| 6,419,704 B1 * | 7/2002 | Ferree .................. 623/17.12 |
| 6,733,533 B1 * | 5/2004 | Lozier .................. 623/17.12 |
| 7,563,284 B2 * | 7/2009 | Coppes et al. ......... 623/17.12 |
| 2002/0123750 A1 * | 9/2002 | Eisermann et al. .......... 606/69 |
| 2003/0040800 A1 | 2/2003 | Li et al. |
| 2007/0093689 A1 * | 4/2007 | Steinberg ................ 600/114 |

FOREIGN PATENT DOCUMENTS

| | | |
|---|---|---|
| EP | 1132061 A2 | 9/2001 |
| WO | 03047472 A1 | 6/2003 |

* cited by examiner

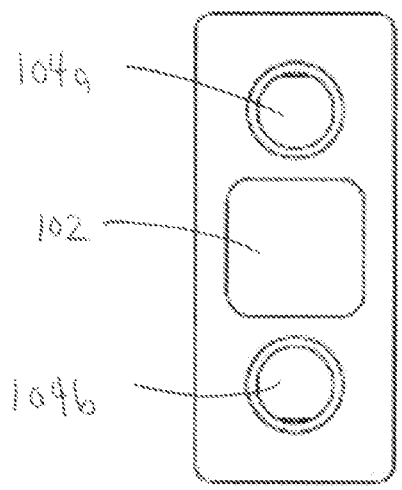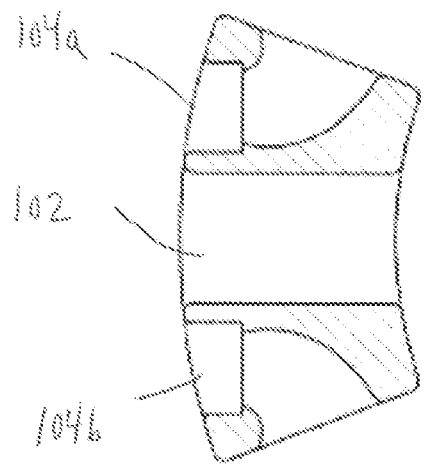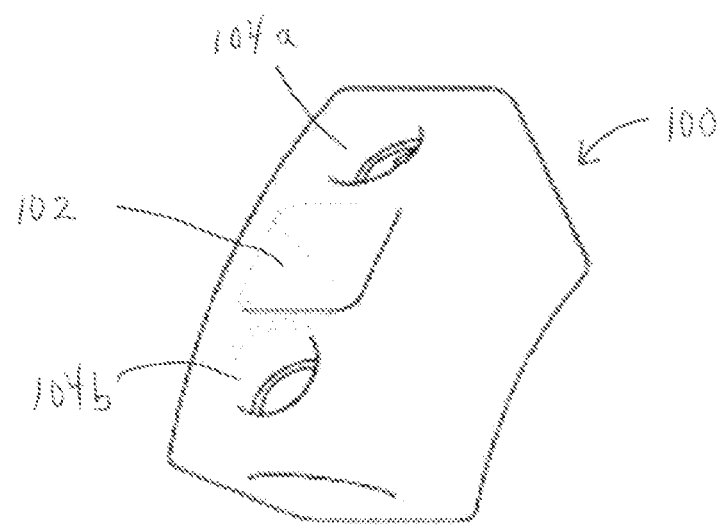
FIG. 10C
FIG. 10B
FIG. 10A

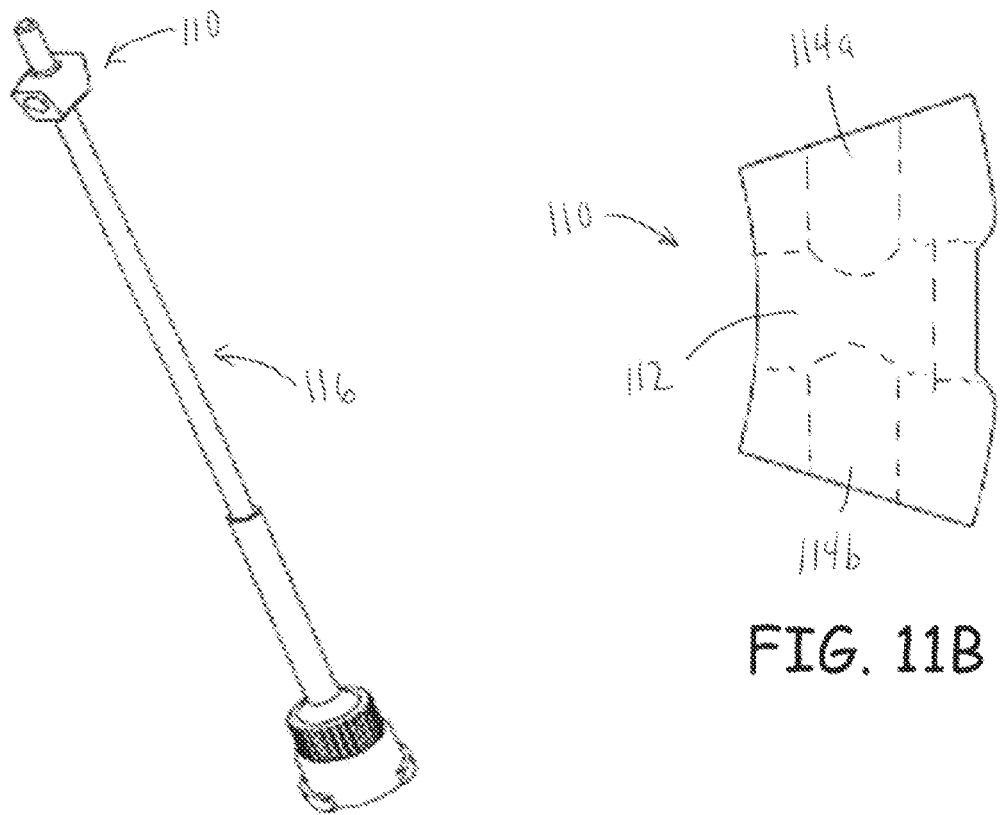
FIG. 11C
FIG. 11B
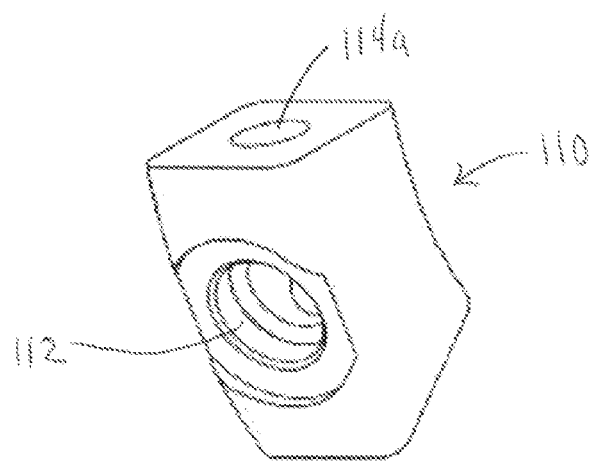
FIG. 11A

INTERBODY FUSION RING AND METHOD OF USING THE SAME

REFERENCE TO RELATED APPLICATION

This application claims the benefit of U.S. Provisional Application No. 60/686,740 filed Jun. 2, 2005, entitled "Interbody Fusion Ring and Method of Using the Same," the entire disclosure of which is incorporated by reference herein.

BACKGROUND

The present invention generally relates to orthopedic implants, and, more particularly, to spinal fusion devices.

When a spinal disc deteriorates one method of treatment is a spinal fusion procedure. Spinal fusion typically involves fusion between two adjacent vertebrae by removing a disc between two adjacent vertebrae and placing a graft material or fusion mass between the vertebrae. The disc includes an annulus which surrounds a nucleus. Surgical access to the disc may be from the anterior or posterior sides (stomach and back) of the patient. The disc is removed from between the two adjacent vertebrae by removing at least a part of the annulus as well as the softer nucleus. A cage is placed between the vertebrae where the disc is removed and a fusion graft or graft mass is packed within the cage and extends between the end plates of the adjacent vertebrae. Rods may also be placed on the posterior side of the spine, with screws attached to a respective rod and extending into a respective vertebrae to stabilize the fusion.

A number of alternative devices for spinal disc treatment are reported.

One alternative device includes rigid, three-dimensional geometric solid devices, either impervious or porous, that function as support struts. When placed in the area of the disc between adjacent vertebral bodies, they allow and/or encourage bone to grow through and/or around the device to cause a bony fusion between two adjacent vertebral bodies. Examples of such devices are reported in U.S. Pat. No. 6,015,436 to Schonhoffer, U.S. Pat. No. 6,010,502 to Bagby, U.S. Pat. No. 5,972,031 to Biedemmann et al., U.S. Pat. No. 5,895,427 to Kuslich, U.S. Pat. No. 5,735,899 to Schwartz et al., U.S. Pat. No. 5,720,748 to Kuslich, U.S. Pat. No. 5,709,683 to Bagby, U.S. Pat. No. 5,700,291 to Kuslich, U.S. Pat. No. 5,669,909 to Zdeblick, U.S. Pat. No. 5,514,180 to Heggeness et al., U.S. Pat. No. 5,591,235 to Kuslich, U.S. Pat. No. 5,489,308 to Kuslich, U.S. Pat. No. 5,489,307 to Kuslich, U.S. Pat. No. 5,405,391 to Henderson et al., U.S. Pat. No. 5,263,953 to Bagby, U.S. Pat. No. 5,059,193 to Kuslich, U.S. Pat. No. 5,015,255 to Kuslich, U.S. Pat. No. 5,015,247 to Michelson, U.S. Pat. No. 4,946,458 to Harms et al., U.S. Pat. No. 4,936,848 to Bagby, U.S. Pat. No. 4,834,757 to Bantigan, U.S. Pat. No. 4,820,305 to Harms et al., U.S. Pat. No. 4,501,269 to Bagby, and U.S. Pat. No. 4,401,112 to Rezaian.

Another alternative device includes semi-rigid artificial joints that allow motion in one or more planes. Examples of these device are reported in U.S. Pat. No. 4,759,769 to Kostuik, U.S. Pat. No. 6,039,763 to Shelokov, and commercially available examples such as the Link device or Charite Intervertebral Disc Endoprosthesis.

Still another alternative device includes non-rigid cushions designed to replace the nucleus of the disc. Examples of artificial discs are described in U.S. Pat. No. 4,904,260 to Ray, U.S. Pat. No. 4,772,287 to Ray and U.S. Pat. No. 5,192,326 to Boa.

Yet another alternative device includes flexible, expandable bags or balloons that become rigid when injected with materials that can support loads. Examples are reported in U.S. Pat. No. 5,571,189 to Kuslich, U.S. Pat. No. 5,549,679 to Kuslich and U.S. Pat. No. 6,332,894.

SUMMARY OF THE INVENTION

The present invention provides an injectable annular ring useful in treating a deteriorating spinal disc. When used, the annular ring may be collapsed or folded in order for it to be placed through a small opening in a prepared intervertebral space within the annulus using minimally invasive techniques. Deployment or unfolding the ring in the intervertebral space provides an interior cavity bordered by the ring that is in direct contact with the vertebral endplates. When an internal volume of the ring is injected or filled with a load-bearing, hardenable material, the filled ring maintains the intervertebral spacing and prevents the ring from being expelled from the interior cavity through the small annular opening.

The present invention includes a number of embodiments. One embodiment is an interbody fusion ring for implanting between adjacent vertebrae. The fusion body provides an injectable annular ring, a web within the internal volume of the ring to control cross-sectional expansion of the ring, at least one access port on an exterior surface of the ring open to the internal volume of the ring, and at least one access port on an exterior surface of the ring open to an interior cavity bordered by the ring. In alternative embodiments, the ring may be a semi-permeable material porous to air and substantially non-porous to an injectable material or fluid. Suitable materials include films, knitted fabrics, woven fabrics or non-woven fabrics.

Another embodiment of the invention is a spinal implant system that includes i) an injectable hollow annular ring including a web within the internal volume of the ring to control cross-sectional expansion of the ring, at least one access port on the ring open to the internal volume of the ring, and at least one access port on the ring open to an interior cavity bordered by the ring; ii) a load-bearing material for injection in to the internal volume of the ring; and iii) an osteobiologic composition for placement in the interior cavity bordered by the ring.

Other embodiments of the spinal implant system may also include a balloon sized and shaped to fit through the access port of the ring into the interior cavity bordered by the ring when the balloon is collapsed. When the balloon is filled with an incompressible fluid and expanded in the interior cavity it serves to decompress surrounding neurological structures or to distract adjacent vertebrae when filled with a fluid.

Further embodiments of the spinal implant system may include at least one injection device to inject the load-bearing material into the internal volume of the ring, to expand a balloon sized and shaped to fit in the interior cavity bordered by the ring, or to inject the osteobiologic composition into the interior cavity bordered by the ring.

Still further embodiments of the spinal implant system of claim may include at least one insertion device to place the ring into an annular space between adjacent vertebrae in a collapsed state and to place a balloon sized and shaped to fit through the access port of the ring into the interior cavity bordered by the ring.

Another embodiment of the present invention is a method of implanting an intervertebral spinal fusion device. The steps of this method may include:

performing a discectomy while preserving an outer annular shell between adjacent vertebrae to provide an intervertebral space;

inserting an injectable annular ring having a web within the internal volume of the ring to control cross-sectional expansion of the ring, at least one access port open to the internal volume of the ring, and at least one access port open to an interior cavity bordered by the ring into the intervertebral space; and directing a load-bearing, hardenable material into the ring in an amount sufficient to fill the ring's internal volume and maintain or distract the intervertebral disc height.

An alternative of this embodiment may include inserting a balloon through the access port of the ring into the interior cavity bordered by the ring, inserting the ring and balloon into the intervertebral space, and filling the balloon to deploy the ring within the intervertebral space and distract the adjacent vertebrae. The filled balloon may also decompress surrounding neurological structures.

Yet another embodiment of the present invention is a spinal implant kit. The components of the kit may include:

an injectable annular ring having a web within the internal volume of the ring to control cross-sectional expansion of the ring, at least one access port open to the internal volume of the ring, and at least one access port open to an interior cavity bordered by the ring;

a load-bearing, hardenable material;

an osteobiologic composition;

a balloon sized and shaped to fit through the access port of the ring into the interior cavity bordered by the ring and to expand in the interior cavity to decompress surrounding neurological structures or distract adjacent vertebrae;

at least one injection device to inject the load-bearing material into the internal volume of the ring, to fill the balloon sized and shaped to fit through the access port of the ring into the interior cavity bordered by the ring, or to inject the osteobiologic composition into the interior cavity of the ring; and at least one insertion device to place the ring and balloon into a space between adjacent vertebrae.

Still another embodiment of the present invention is a method of fusing adjacent vertebrae. This method may include:

accessing adjacent vertebrate to be fused;

performing a partial or complete discectomy;

creating an intervertebral space having top and bottom vertebral endplate surfaces;

preparing the top and bottom end plates for fusion;

inserting a balloon through an access port of injectable annular ring having a web within the internal volume of the ring to control cross-sectional expansion of the ring, at least one access port open to the internal volume of the ring, and at least one access port open to an interior cavity bordered by the ring;

collapsing the balloon and ring;

inserting the balloon and ring into the intervertebral space;

filling the balloon with an incompressible fluid to deploy the ring and decompress surrounding neurological structure or distract the adjacent vertebrae;

injecting the ring with a load-bearing, hardenable material;

hardening the load-bearing material;

removing the fluid from the balloon;

removing the balloon from the interior cavity of the ring;

filling the interior cavity of the ring with an osteobiologic composition; and, optionally, sealing the access port to retain the osteobiological composition within the cavity.

DESCRIPTION OF THE DRAWINGS

FIGS. 10a-10d illustrate an embodiment of an access port.

FIGS. 11a-11c illustrate another embodiment of an access port.

DETAILED DESCRIPTION

Figure 1:
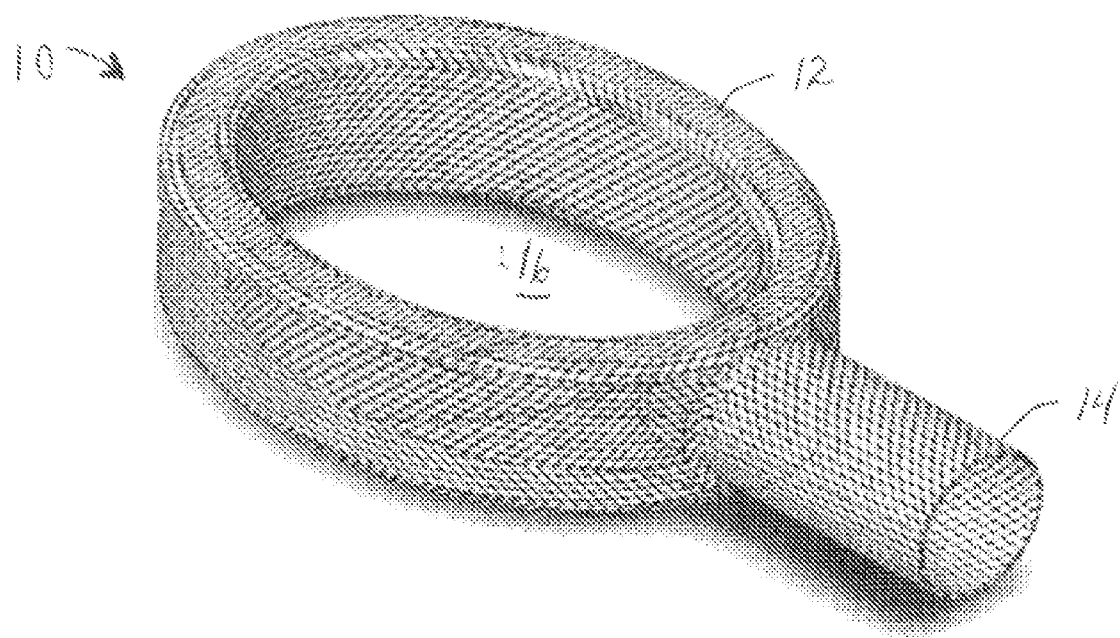
FIG. 1 is a perspective view of a textile structure for use as an interbody fusion ring.

FIG. 1 is a perspective view of one embodiment of an interbody fusion ring (IFR) for use in fusing adjacent vertebrae. FIG. 1 illustrates an IFR 10 formed of a film, woven, non-woven or knitted tube 12. Suitable fabric materials may be made from monofilament or multifilament threads or yarns with the threads or yarns made from polyacrylates, polyethylene, polypropylene, polyolefin copolymers, polycarbonates, polyesters, ether-ketone copolymers, polytetrafluoroethylene fibers or silk. Other suitable materials that may be used to form the IFR are reported in published application US 2004-0230309, which is incorporated by reference herein. In some embodiments at least a portion of the threads or yarns comprise consolidated, partially consolidated or heat set threads or yarns.

The interior cavity of the IFR 10 defines or forms an interior cavity or open center 16, into which an osteobiological composition or material, such as a bone growth material, may be placed. Because the IFR 10 may be formed from a fabric material, it may be collapsed or folded and deployed using an insertion device such as a small catheter. Once in place, an access port 14 on an exterior surface of the ring allows for an internal volume of the IFR to be filled with any suitable load-bearing material, such as bone cement, so that the side walls of the textile structure can, in part, stabilize the adjacent vertebral bodies for fusion.

Suitable load-bearing materials may include poly(lactic acid), poly(glycolic acid), p-dioxanone fibers, polyarylethyl, polymethylmethacrylate, polyurethane, amino-acid-derived polycarbonate, polycaprolactone, aliphatic polyesters, calcium phosphate, unsaturated linear polyesters, vinyl pyrrolidone, polypropylene fumarate diacrylate, or mixtures thereof. Particular examples of suitable load-bearing materials that may be used to fill the IFR 10 are polymethylmethacrylate (PMMA) or a bis-GMA polymer. Other suitable load-bearing materials are reported in published application US 2004-023039, which is incorporated by reference herein.

The IFR ring 10 is dimensioned to provide the necessary structure for stabilizing vertebral bodies for fusion so that the fabric structure conforms to anatomic sagital and frontal planes, as well as other anatomic planes, the are perpendicular to the anatomic traverse plane. The IFR 10 may take any of a number of ranges of possible eccentricity dimensions. Specifically, the eccentricity ratio of the IFR 10 may range from about 1.0-2.2. Further, the ring major and minor axis may range from about 27×20 mm to about 50×37 mm. The typical height range for side walls is about 5-15 mm. The length of the access portal may be of any suitable length, and is preferably flush with the fabric wall of the ring. The thickness of the side wall may take any suitable thickness, and may be in a range of about 0.1-3 mm. Further, the dimensions of the tube which forms the ring 10 may be any suitable size. For example, the height of the sidewall tube may be between about 5-15 mm, and the width of the tube may be about 3-8 mm.

The IFR ring 10 may be formed of a three dimensional textile material. Such three dimensional fabrics are particularly suited for use as the IFR ring 10 because of the three dimensionally interconnected porosity of the fabric. When either coated or filled with a hardenable, load-bearing material, such as PMMA, the woven IFR ring 10 forms a composite structure with the coating or fill material. The coating or fill material is able to flow into the interconnected pores of the IFR ring 10 and encapsulate the fibers over most or all of the thickness of the fabric wall because of the interconnected porosity.

One suitable three dimensional textile is a honeycomb fabric available from Offray Specialty Narrow Fabrics of Chester, N.Y. This honeycomb weave has a three-dimensional, non-orthogonal, cell-like structure of multifilament yarns. Long floats form the periphery of the cells. The interlacing is progressively tightened, toward the cell center, with the tightest interlacing occurring at the center of the cell. This weave pattern creates a structure of hollow pockets between raised portions, similar to a honeycomb or waffle. The face and the back of the fabric look alike, the midpoint of the cell on one side serving as the outer corner on the other side. In other words, the high point on one side of the fabric is the low point on the other side.

The access portal 14 is shown in FIG. 1 as being constructed for a straight lateral approach, with the access portal 14 aligned with the major axis of the device 10. However, the device is not so limited, and the access portal 14 may be placed in any suitable location.

Figure 2:
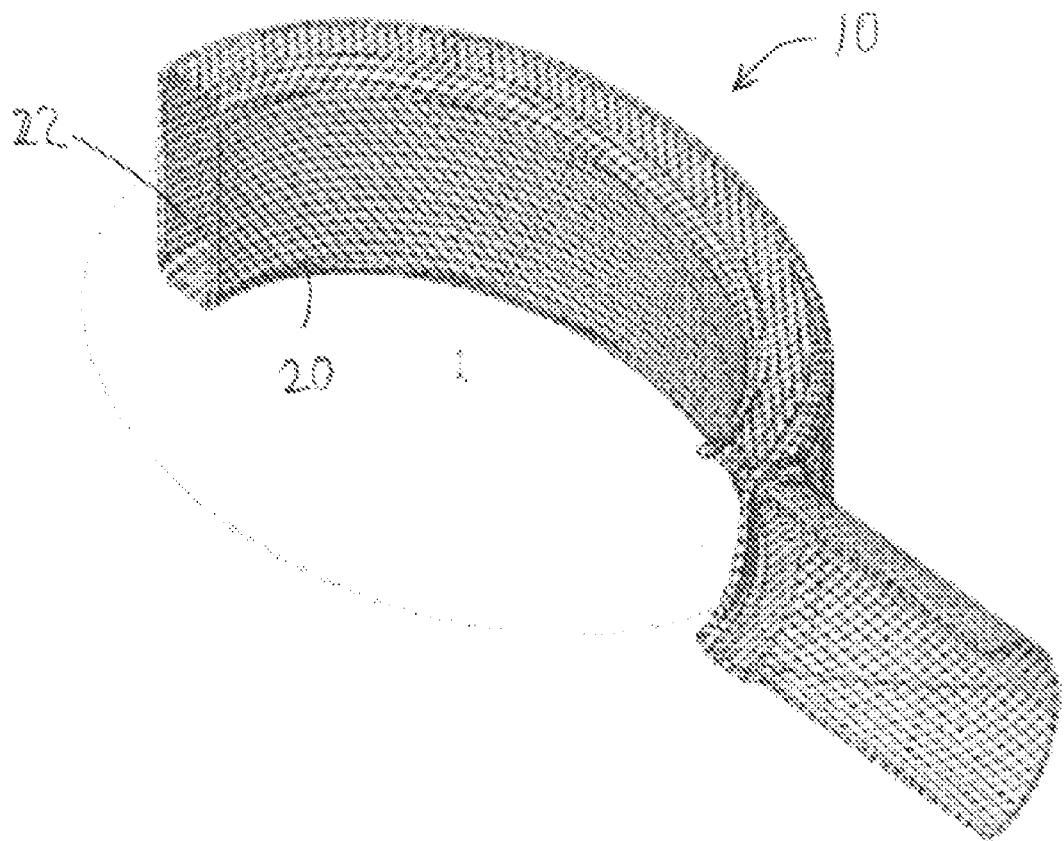
FIG. 2 is a partial cross sectional view of a textile structure for use as an interbody fusion ring.

FIG. 2 is a partial cross sectional view of the IFR ring 10. The IFR ring comprises a wall 20 which surrounds an internal volume 22. The IFR 10 is designed to hold pressure applied by injecting or filling the internal volume 22 with a suitable material, such as a PMMA bone cement. When filled, the IFR 10 is capable of sustaining the internal pressure of the fill material, providing a shape to the material as it cures, and preventing any substantial escape of the material from the internal volume of the ring.

The construction and pressure holding capability of the IFR 10 will allow the IFR 10 to expand substantially in the vertical direction under fill or inflation pressure from the injected material. The IFR's vertical expansion will decompress surrounding neurological structures and provide and maintain distraction of the spine segment. Distraction is thought to be desirable for fusion to establish tension bands in the natural tissues for segment stability and for aid in decompressing nervous tissues in the central spinal canal and the root canals. Clinical distraction loads on the spine can reach 200 N (45 lb$_f$) or more based on published intradiscal pressures in supine and prone positions and on relative cross-sectional areas of the nucleus and annulus. Thus, the IFR 10 must be capable of maintaining an injection pressure of approximately 0.62 MPa (90 psi) to distract against the intraoperative load of 200 N given the IFR's geometric parameters discussed above.

The IFR ring 10 may be constructed so that the textile material or fabric is a filter that is permeable to air or gas but relatively impermeable to the flow of the material used to fill the IFR ring 10. When the fill material is a bone cement, the impermeability of the IFR ring 10 will allow the annular ring to maintain pressure in a manner similar to an annular shaped balloon. The IFR 10 will be capable of decompressing surrounding neurological structures and distracting the disc space because of its ability to hold pressure until the bone cement cures. Distraction is expected to create tension bands from the natural annulus and surrounding ligaments to help stabilize the motion segment until fusion throughout the fusion graft material occurs.

The IFR 10 may be used in conjunction with posterior instrumentation for a fusion construct. The advantage of using the IFR 10 deployed to the interbody space, along with posterior instrumentation is that the fusion can be performed without having to perform both an anterior and a posterior procedure.

Figure 3A:
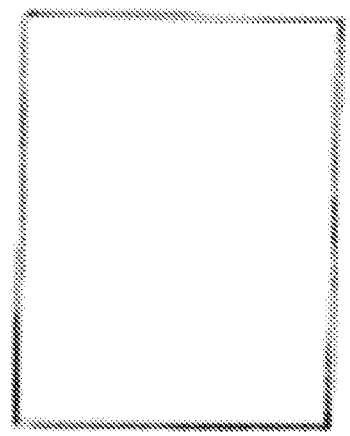
FIGS. 3A and 3B illustrate cross-sectional views of an interbody fusion ring.
Figure 3B:
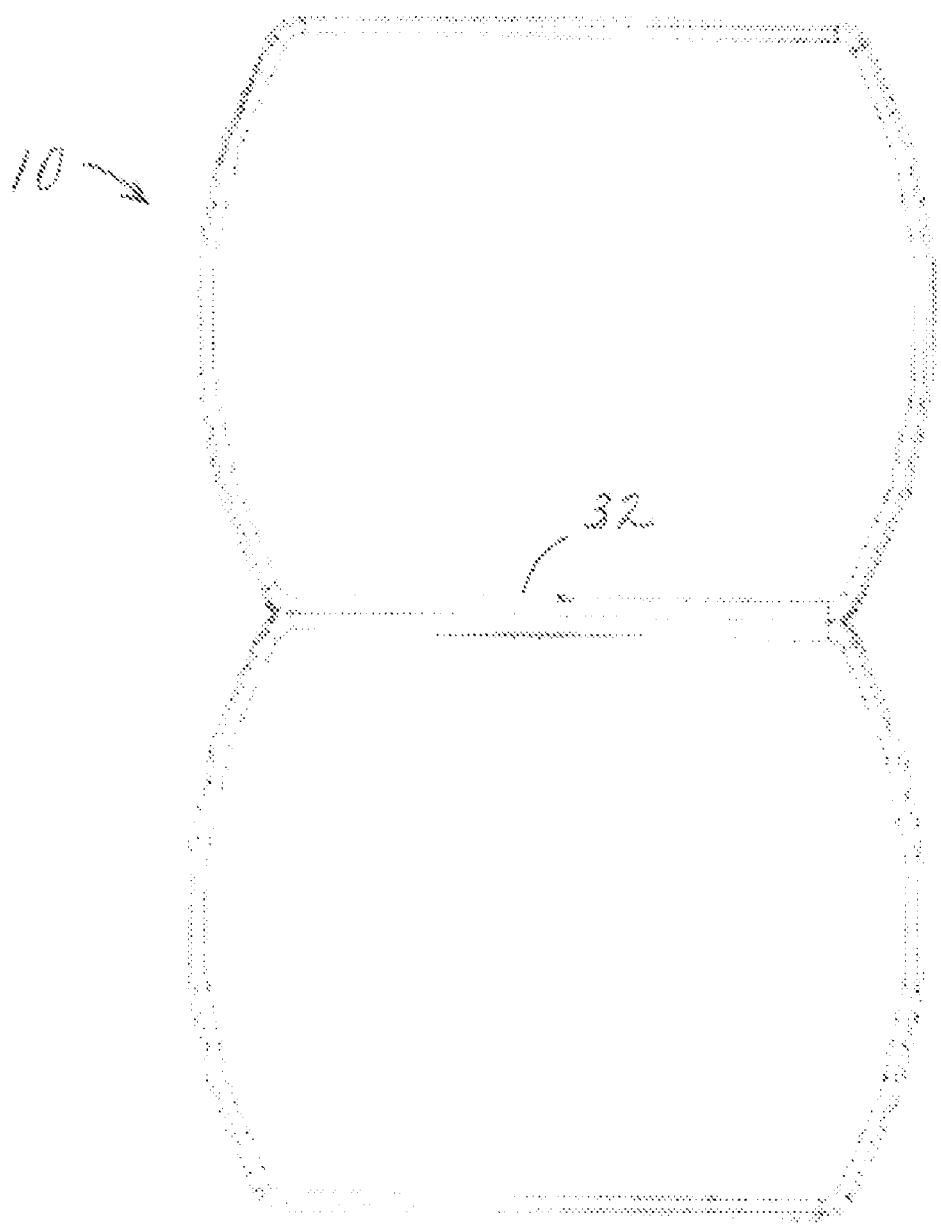

FIGS. 3A and 3B illustrate cross-sectional areas suitable for the textile structure used to form the IFR ring. As shown in FIG. 3A, the IFR may be formed as a tube. Further, as shown in FIG. 3B, the IFR may be formed as a tube having an internal web or webbing 32 to help maintain a desired geometry once the IFR is filled with material. The internal web 32 may take any suitable shape or design, and is intended to provide the desired structural support to the IFR 10 once it is filled or being filled with material to cause the vertical expansion normal or transverse to the horizontal mid-plane of the IFR to exceed the radial expansion of the IFR. Though FIG. 3B illustrates a web 32 across the middle of the tube, the web 32 is not so limited.

The web may be formed from a variety of materials including films, knitted fabrics, woven fabrics, non-woven fabrics, fibers, threads or yarns. In one embodiment, the web is a structure of stitched fibers or yarns that are placed along the length of a suitable woven fabric tube. In another embodiment, the web is a structure of woven threads or yarns that are woven into place during a weaving process used to form a suitable tube that may be used to form the ring.

In some embodiments, the ring and web may be coated with a flexible coating. The coating may serve a number of functions including forming a composite with a three-dimensional material (as described above with respect to the load-bearing materials), or sealing the ring to form a semi-permeable or porous structure that is porous to air or gas but is non-porous to a filling material. The coating may also be selected to promote filling the internal volume of the ring with an injectable fluid. Still further, the coating may be selected to act as a thermal insulating material. Suitable flexible coatings include hydrogels, thermoset or thermoplastic urethanes, thermoset or thermoplastic elastomers, polytetrafluoroethylene fibers, polysiloxanes, polyvinylalcohols, proteins, or collagen.

Figure 4A:
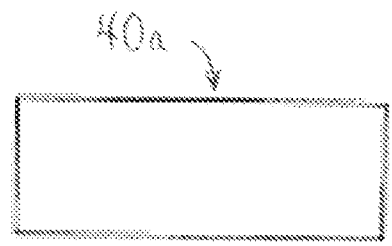
FIGS. 4A and 4B are side views illustrating shapes of an interbody fusion ring.
Figure 4B:
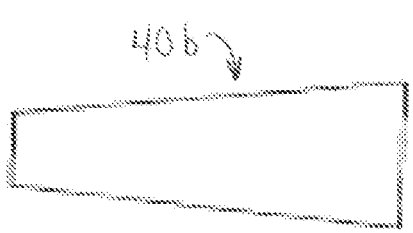

FIGS. 4A and 4B are side views of alternative shapes of IFRs 40a and 40b. As illustrated in FIG. 4A, the IFR 40a is constructed so that the top and bottom surfaces have parallel planes. As illustrated in FIG. 4B, the IFR 40b is constructed in a wedge shape to obtain lordosis.

FIGS. 5-8, 10a-10d, 11a-11c and 12a-12b illustrate various designs for the access ports of the IFR.

Figure 5:
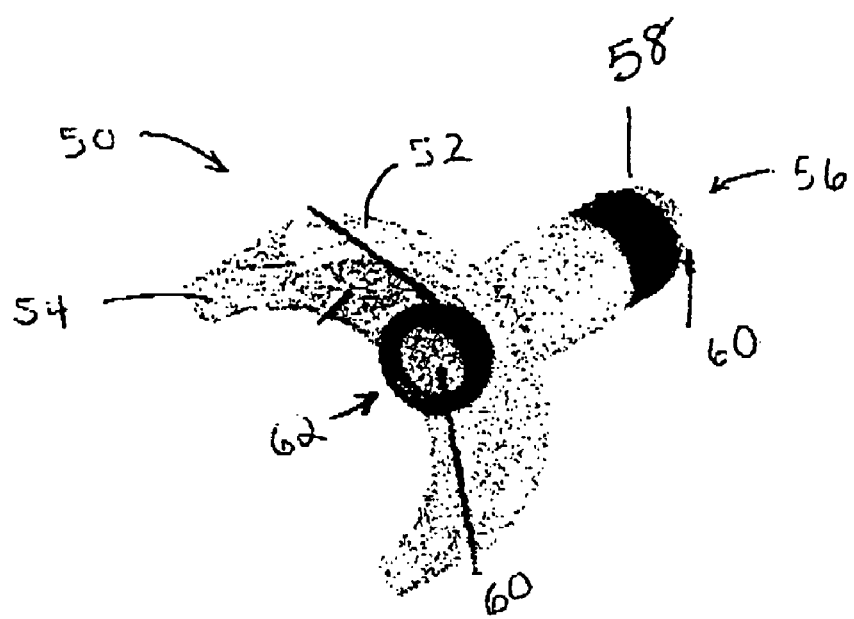
FIG. 5 is a partial perspective view of an interbody fusion ring having a delivery cannula attached.

FIG. 5 is a partial perspective view of one embodiment of an IFR 50. FIG. 5 illustrates a ring portion 52 having open or hollow internal volume 54. An access port 56 is provided, through which a polymer injection device, such as a delivery cannula 58 and/or inner sleeve 60 can be placed. As shown in FIG. 5, the injection device 58 and sleeve 60 are co-axially aligned.

In some embodiments, the injection device 58 is used to deliver the IFR into the disc space, and later is used to deliver bone growth material to the interior cavity formed inside the IFR 50. The delivery cannula 58 provides access across the IFR 50 to the interior cavity, and thus passes through a hole 62 in the back wall of the IFR 50. The inner sleeve 60 is used to deliver polymer to the hollow internal volume 54 of the IFR 50. As such, the inner sleeve 60 is interconnected with the internal volume 54 of the IFR 50 in any suitable way that will allow for the flow of bone cement, PMMA, or similar material to flow into the hollow internal volume 54 of the ring 50.

Once the PMMA or bone cement material has begun to harden, the inner sleeve 60 may also be used to cut the PMMA between the ring and the injection device to allow the delivery sleeve 60 to be removed, and allow access to the fusion area. For instance, the delivery sleeve 60 may simply be rotated a full turn, or any suitable amount, to separate the PMMA located in the internal volume of the ring 50 from that left in the delivery sleeve 60. Once separated, it becomes easier to remove the delivery sleeve 60 so that the next step, filling the area inside the IFR ring with bone growth material, may begin.

Figure 6:
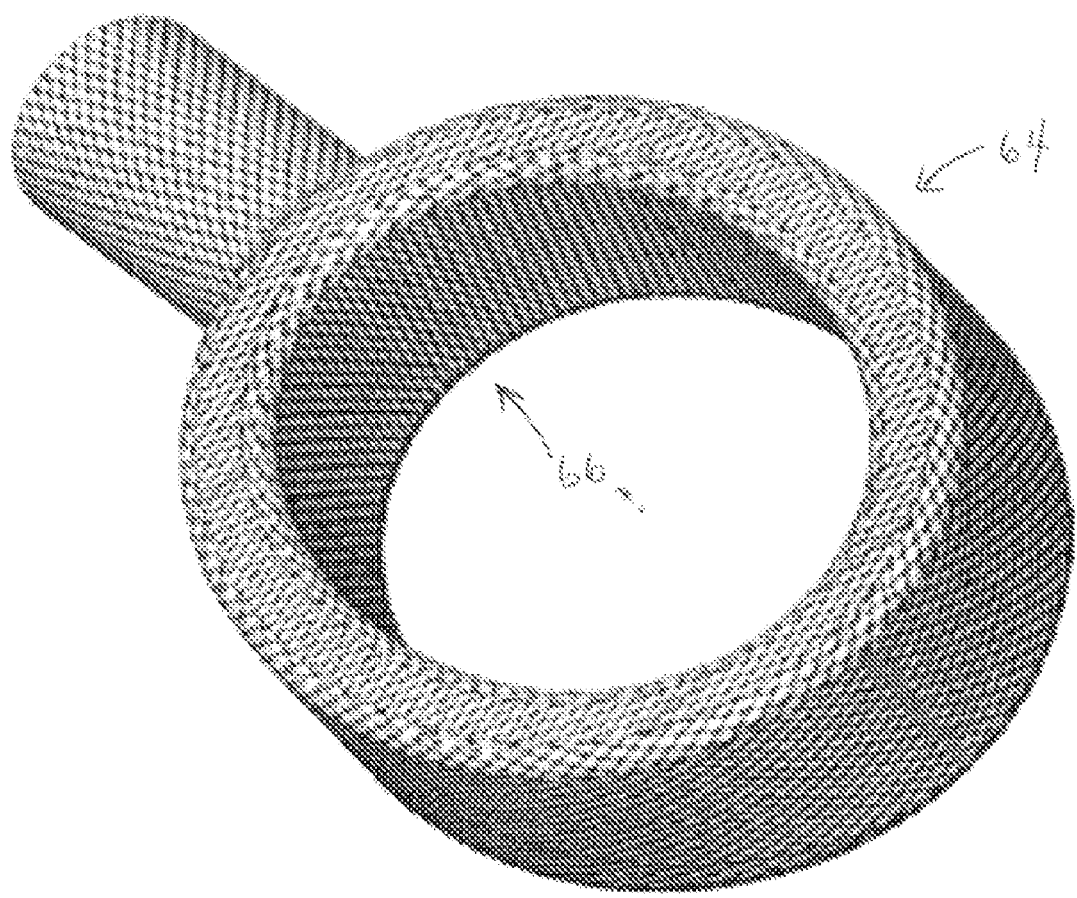
FIG. 6 is a perspective view of an alternate embodiment of a textile structure for use as an interbody fusion ring.

FIG. 6 illustrates another embodiment of an IFR 64. In FIG. 6, the IFR is formed having a solid back wall 66 having a continuous, smooth geometry with the inside surface of the IFR. Forming the IFR 64 with a solid back wall 66 reduces the risk that the fill material will leak at a port or hole created to allow access through the IFR to the inner cavity of the ring. To access the interior cavity to fill it with bone growth material, it may be necessary to first pierce the back wall 66.

Figure 7:
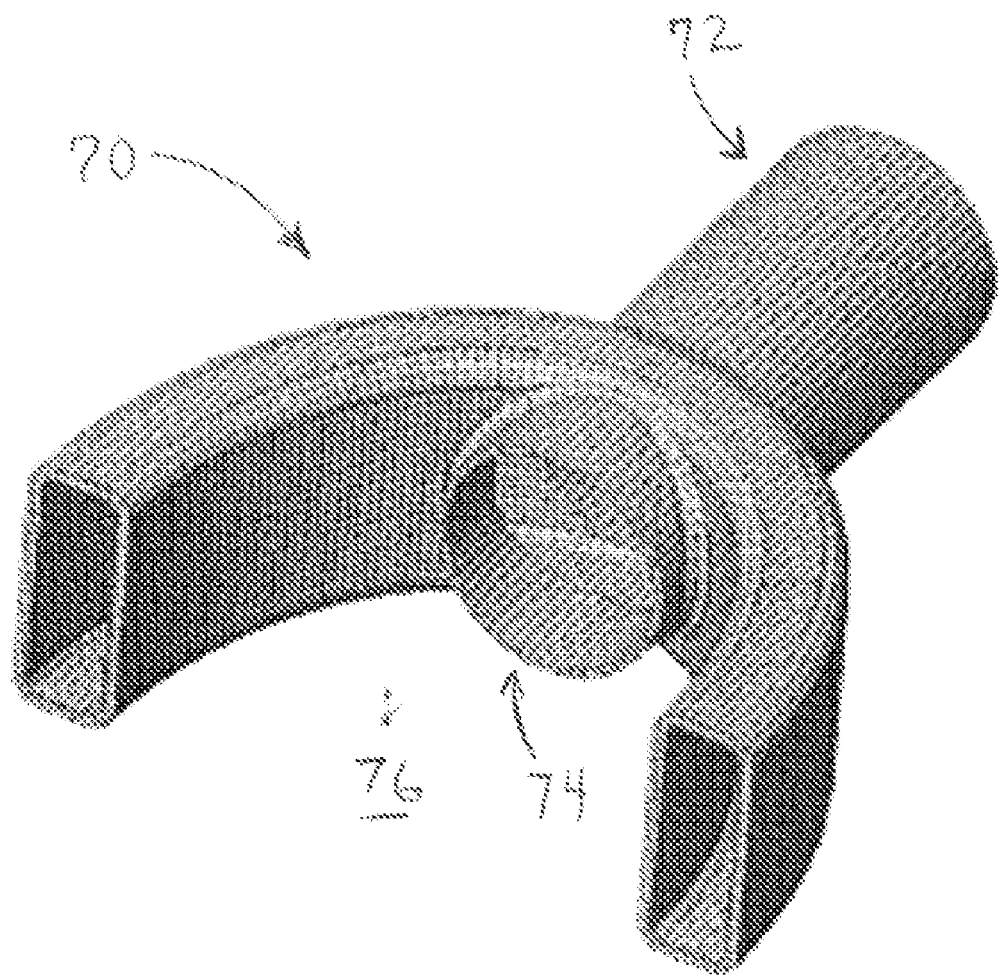
FIG. 7 is a partial perspective view of an alternate embodiment of a textile structure for use with an insertion device.

FIG. 7 illustrates yet another embodiment of an IFR 70. FIG. 7 illustrates a portion of an IFR 70 having a port 72. The port 72 further comprises an extension 74 which extends into the interior cavity 76 of the ring. The fabric extension 74 may be open or closed on its back surface where the arrow is shown in FIG. 7. Forming an extension 74 on the access port 72 which extends into the ring's interior cavity 76 allows the material of the extension 74 to be folded back into an injection device such as a delivery cannula (not shown). When folded back into the delivery cannula, the material of the extension 74 is sandwiched between the delivery cannula lip and the bottom surface of the inner sleeve so that the material of the extension 74 forms an edge with an internal sleeve and creates a tight seal. The bottom of the inner sleeve can be mated for a sealing fit to the delivery cannula lip. This sealing concept would form a tube extension 74 or a "sock" like structure for the delivery cannula if the extension 74 is closed off to the ring's interior cavity 76. The fabric extension 74 may be made as a single piece of woven fabric, or may be made by connecting a separate port portion to the ring 70 using any suitable method, such as suturing.

Figure 8:
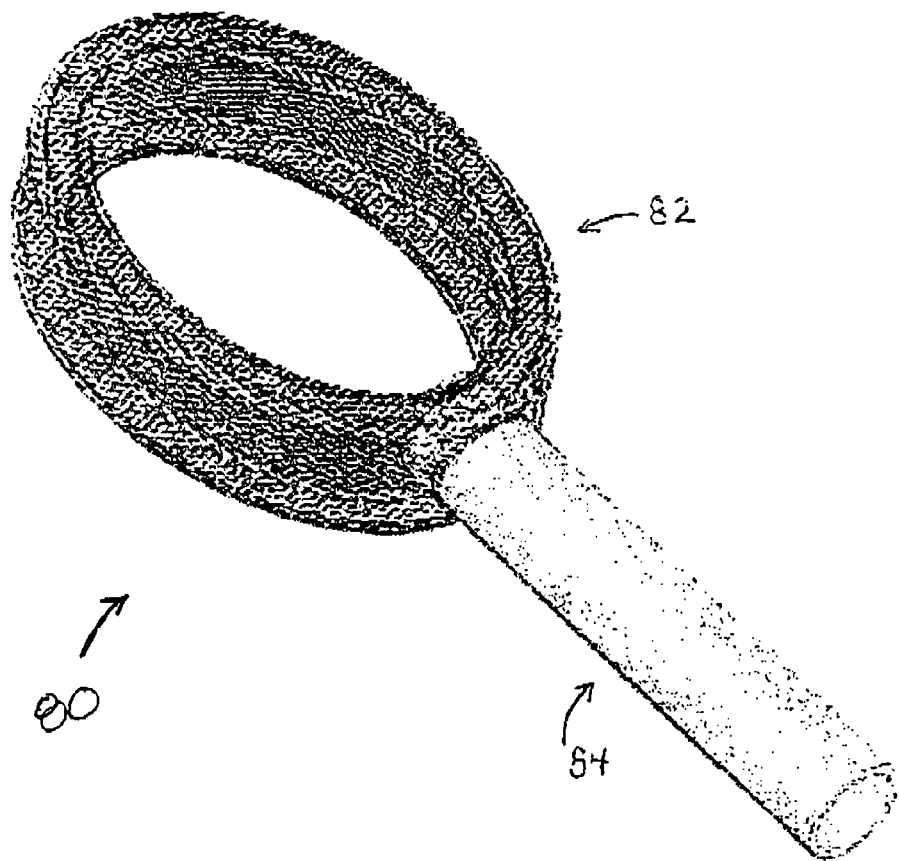
FIG. 8 is a perspective view of an alternate embodiment of a textile structure for use as an interbody fusion ring having a solid access port.

FIG. 8 is a perspective view of an alternate embodiment of a textile structure for use as an IFR. Shown in FIG. 8 is an IFR 80 comprising a textile ring 82 having a solid access port 84 on an exterior surface of the ring. The length of the solid port 84 is any suitable length, and preferably is between about 5-250 mm. A longer length may be useful in that the solid port 84 may be used to connect the IFR 80 to a polymer pumping device, such as PMMA pump. The solid port 84 may be formed of any suitable material, such as PET or PBT. Preferably, the solid port 84 is formed of a material that is compatible with the material used to form the textile structure 82.

The solid port 84 may be attached to the ring 82 using any suitable method, such as heat bonding, suturing, or use of an adhesive. Heat bonding is a particularly suitable method of joining the tube port 84 and the IFR textile ring 82. In this case, the port 84 would not be made of fabric and only a short fiber land would be needed to contact the solid port 84 from the IFR ring 82 for heat bonding. The port tube 84 could be injection molded or blow molded to obtain the desired features.

Figure 10D:
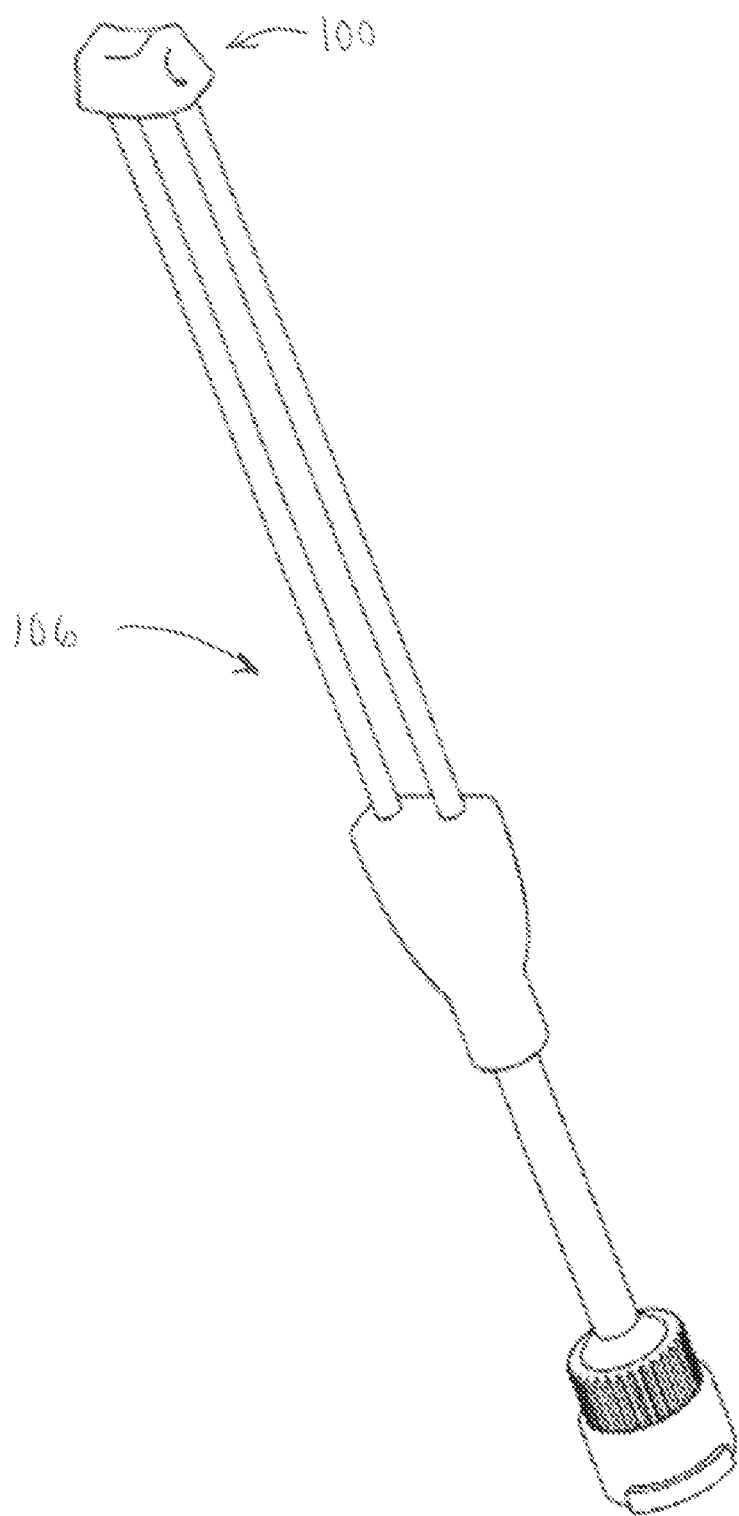

FIGS. 10*a*-10*d* illustrate an alternative embodiment of an access port on the exterior surface of the ring of the present invention. FIG. 10*a* is a perspective view of parallel port structure 100. Parallel port 100 has first aperture 102 providing connection to the interior cavity bordered by an attached ring (not shown) and has second apertures 104*a* and 104*b* providing a connection to an internal volume of the ring. The configuration of these apertures is further illustrated in a front view of the port, FIG. 10*b*, and in a cross-section view of the port, FIG. 10*c*. FIG. 10*d* illustrates a partial view of an injection device 106 that may be used to inject a load-bearing material into the internal volume of the ring through apertures 104*a* and 104*b*.

Figure 13:
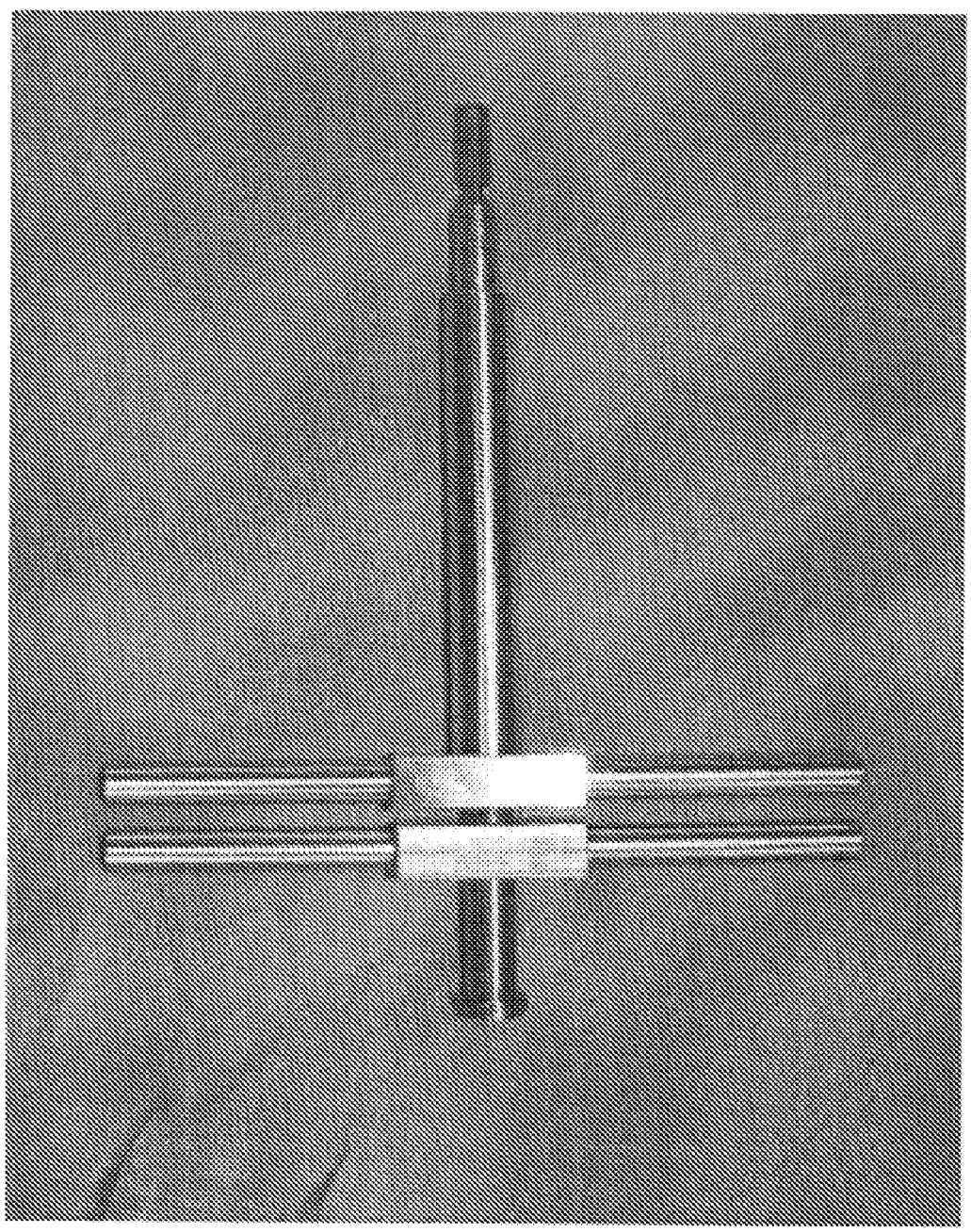
FIG. 13 illustrates an embodiment of an insertion device.

FIGS. 11*a*-11*c* illustrate still another embodiment of an access port on the exterior surface of the ring of the present invention. FIG. 11*a* is a perspective view of a coaxial port structure 110. Coaxial port 110 has first aperture 112 providing a connection to the interior cavity bordered by an attached ring (not shown) and second apertures 114*a* and 114*b* providing a connection to an internal volume of the ring. FIG. 11*b* further illustrates, in phantom, the configuration of these apertures. FIG. 11*c* illustrates a partial view of an injection device 116 that may be used to inject a load-bearing material into the internal volume of the ring through apertures 114*a* and 114*b*. Injection device 116 is configured to provide a fluid connection to apertures 114*a* and 114*b* that is independent of a fluid connection to aperture 112 while maintaining a second fluid connection to the interior cavity of the ring. The second fluid connection may be used to fill a balloon that may be inserted into the interior cavity of the ring when the balloon is attached to the injection device. FIG. 13 illustrates an injection device that may be used with the coaxial port structure 110.

Figure 12A:
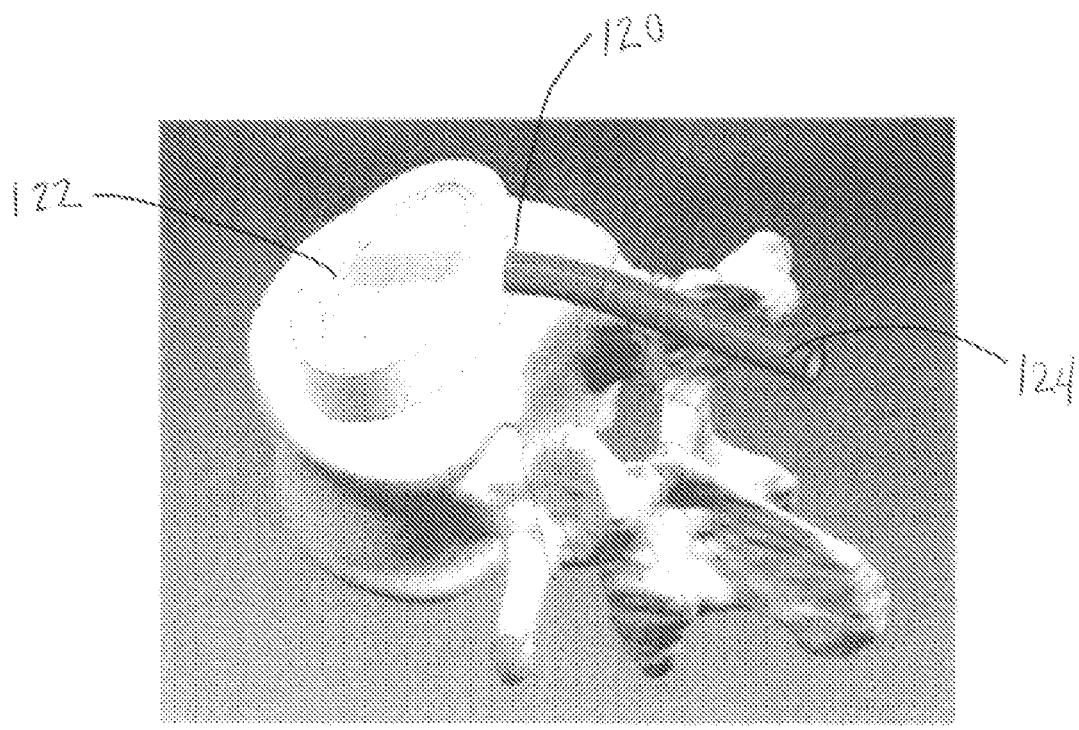
FIGS. 12a and 12b illustrate an embodiment of a two-part access port system.
Figure 12B:
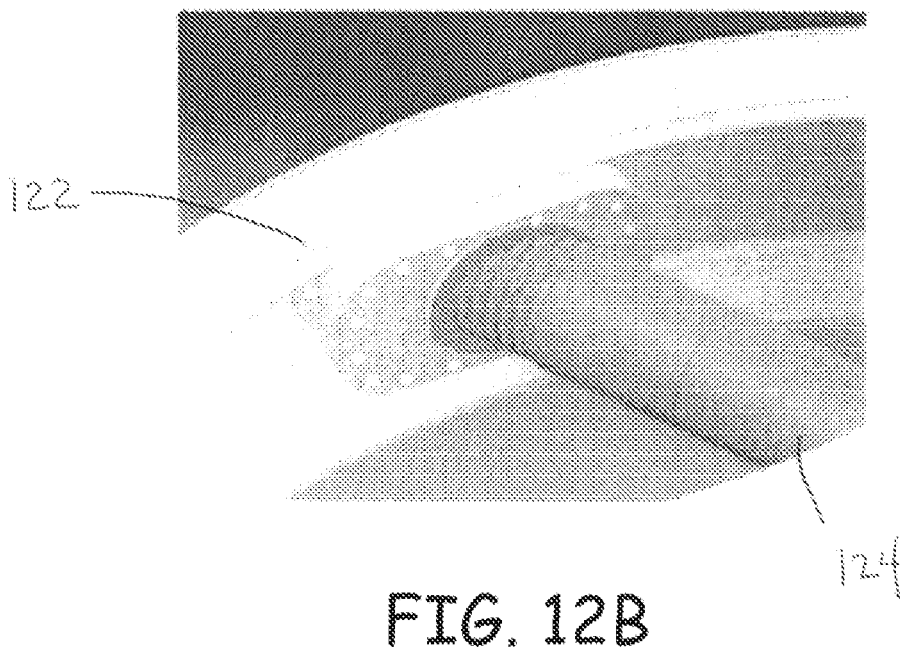

FIGS. 12*a* and 12*b* illustrate yet another access port on the exterior surface of the ring of the present invention. FIG. 12*a* is a perspective view of a two component access port. The first port 120 provides a sealed port providing access to the interior cavity of the ring. The port is sealed to the internal volume of the ring. The second port 122 connects to the internal volume of the ring. The second access port 122 connected to an injection device 124 is illustrated in FIG. 12*b*. In use, a balloon is fitted to an outer cannula that can be inserted through the first port 120 into the interior cavity of the ring. An inner cannula may be fitted to the second port 122 in order to inject a hardenable, load-bearing material into the internal volume of the ring. The inner and outer cannula allow the balloon to be filled with a fluid while the material is injected into the internal volume of the ring. After the material has hardened, the fluid in the balloon may be removed, the balloon collapsed and then removed through the first port 120.

Figure 9:
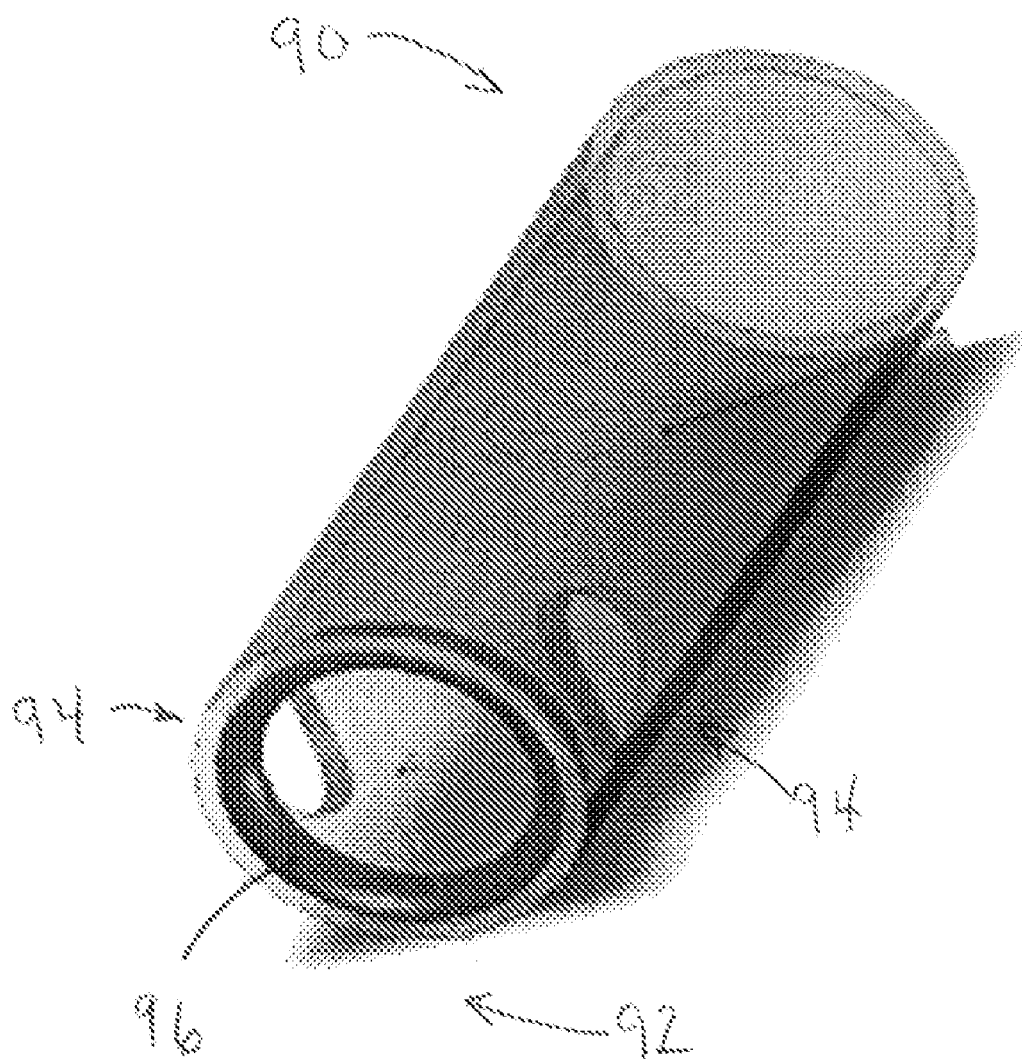
FIG. 9 is a perspective view of an insertion device.

FIG. 9 is a perspective view of one embodiment of an insertion device such as a delivery cannula suitable for use with the present invention. FIG. 9 illustrates a portion of a cannula 90 having a distal end 92. Located on the distal end 92 are side holes 94 and a seal 96. The side holes 94 are used to direct the flow of polymer material through the cannula 90 and into the internal volume of the IFR. The seal 96 is an area which helps to create a tight fit so that material pumped into the IFR ring enters the interior volume of the ring, rather than leaking into the newly created cavity in the disc space.

The seal 96 may take any suitable form. In one embodiment, the seal 96 is in the form of a lip which creates a positive stop. When filling the interior of the IFR ring with material such as PMMA, the seal is pressed against the back wall of the IFR ring in an effort to minimize any leakage of the PMMA from the area where the delivery cannula 90 contacts the back wall surface of the port.

The cannula 90 may be made of suitable material, such as polymer or metal, and may be made using any suitable method, such as by injection molding, blow molding, or machining. For either the integrated port tube 84 (FIG. 8) or the cannula 90 (FIG. 9), other features of the delivery cannula portion may include the port holes, a distal positive stop ring or lip to ensure the port or cannula does not extend too far through the IFR, and potentially a snap attachment to retain an inner sleeve into the port. Such an attachment would alleviate the need for a locking collar and the solid port tube would eliminate the need for the PMMA delivery cannula.

The following features provide, in part, the IFR's functional ability to aid in achieving a fusion:

distraction against intraoperative spinal loads;

ability to substantially retain the hardenable, load-bearing material inside of the annular ring structure until the material cures;

ability to provide a shape to the hardenable, load-bearing material; and support a substantial portion of the spinal load transmitted through the vertebral bodies and share the load with posterior instrumentation.

These features provide, in part, using the injectable annular ring to treat a deteriorating spinal disc that has means for placing the annular ring in a collapsed or folded state through a small annular opening into an intervertebral space within the annulus having prepared vertebral endplates using minimally invasive techniques; means for deploying or unfolding the annular ring in the intervertebral space having a sufficient foot print to prevent substantial penetration of the endplates and to provide an interior cavity bordered by the ring that is in direct contact with the vertebral endplates; and means for injecting an internal volume of the annular ring with a load-bearing, hardenable material to maintain intervertebral spacing and prevent the ring from being expelled from the intervertebral space through the small annular opening.

Another embodiment of the invention is a spinal implant system that includes:

an injectable hollow annular ring including a web within the internal volume of the ring to control cross-sectional expansion of the ring, at least one access port open to the internal volume of the ring, and at least one access port open to an interior cavity bordered by the ring;

a load-bearing material for injection into the internal volume of the ring; and an osteobiologic composition for placement in the interior cavity bordered by the ring.

Suitable osteobiological composition include natural or synthetic graft substance promoting fusion of adjacent vertebrae. Particular examples of these compositions include mesenchymal stem cells, growth factors, cancellous bone chips, hydroxyapatite, tri-calcium phosphate, polylactic acid, polyglycolic acid, polygalactic acid, polycaprolactone, polyethylene oxide, polypropylene oxide, polysulfone, polyethylene, polypropylene, hyaluronic acid, bioglass, gelatin, collagen or polymeric fibers. Other suitable osteobiological compositions are reported in published Application US 2004-0230309, which is incorporated by reference herein.

In alternative embodiments, the spinal implant system includes a balloon sized and shaped to fit through the access port of the ring into the interior cavity bordered by the ring in a collapsed state. When the balloon is filled with a fluid, it may be used to deploy the ring, decompress surrounding neurological structures and distract adjacent vertebrae.

In still other embodiments the spinal implant system includes at least one injection device to inject the load-bearing material into the internal volume of the ring, to expand a balloon sized and shaped to fit in the interior cavity bordered by the ring, or to inject the osteobiologic composition into the interior cavity bordered by the ring. The spinal implant system may also include at least one insertion device to place the ring in a collapsed state into an annular space between adjacent vertebrae.

Another embodiment of the invention is a surgical kit for implanting the IFR ring. The components of the kit include the implant, comprising the IFR and load-bearing material, such as a PMMA bulk polymer, along with suitable injection and insertion devices allowing the annular ring to be properly placed, deployed and injected or filled, and allowing the interior cavity to be properly filled.

In one embodiment, the spinal implant kit components include:

an injectable annular ring having a web within the internal volume of the ring to control cross-sectional expansion of the ring, at least one access port open to the internal volume of the ring, and at least one access port open to an interior cavity bordered by the ring;

a load-bearing, hardenable material;

an osteobiologic composition;

a balloon sized and shaped to fit through the access port into the interior cavity bordered by the ring and to expand in the interior cavity to distract adjacent vertebrae;

at least one injection device to inject the load-bearing material into the internal volume of the ring, to fill a balloon sized and shaped to fit through the access port of the ring into the interior cavity bordered by the ring, or to inject the osteobiologic composition into the interior cavity of the ring; and at least one insertion device to place the ring and balloon into a space between adjacent vertebrae.

One embodiment of the present invention is a method of implanting an intervertebral spinal fusion device. The method includes:

performing a discectomy while preserving an outer annular tissue between adjacent vertebrae to provide an intervertebral space;

preparing exposed vertebral end plates for fusion;

inserting an injectable annular ring having a web within the internal volume of the ring to control cross-sectional expansion of the ring, at least one access port open to the internal volume of the ring, and at least one access port open to an interior cavity bordered by the ring; and directing a load-bearing, hardenable material into the internal volume of the ring in an amount sufficient to fill the internal volume of the ring.

In an alternative of this embodiment, a balloon is inserted through the access port of the ring into the interior space into the interior cavity bordered by the ring and both the balloon and ring are then inserted into the intervertebral space. Once inserted, filling the balloon serves to deploy the ring within the intervertebral space, decompress surrounding neurological structures and distract the adjacent vertebrae. Following this procedure, the ring may be filled with a load-bearing material which is allowed to harden. After the material is hardened, the balloon may be removed from the interior of the cavity and the cavity may then be filled with an osteobiologic composition.

One embodiment of the present invention is a method of treating a patient having a deteriorating spinal disc. This method includes:

accessing the deteriorated spinal disc;

using minimally invasive techniques to place a collapsed or folded annular ring through a small opening into an intervertebral space within the annulus having prepared vertebral endplates;

deploying the ring in the intervertebral space to provide an interior cavity bordered by the ring that is in direct contact with the vertebral endplates;

injecting a load-bearing hardenable material into an internal volume of the ring to maintain intervertebral spacing and prevent the ring from being expelled from the intervertebral space through the small annular opening; and filling the intervertebral space with an osteobiologic material that is in direct contact with the prepared vertebral endplates.

In one embodiment this method, the surgical approach is a paraspinal approach with midline incision. The paraspinal approach is desirable because this posterior approach technique will allow direct visualization of landmark structures, nervous tissues, the posterior annular wall, and potential sequestered fragments from a herniation. The approach allows bilateral access to the disc space for nuclectomy if the physician desires. The IFR itself could be placed into the disc space through a small access of probably 6 mm to 7 mm diameter. The IFR may be a stand alone device, or may be used in connection with additional instrumentation. When used with additional instrumentation, a larger incision for the paraspinal approach is dictated by the need for placing posterior instrumentation. However, any suitable approach may be used. Other MIS techniques could be used for placing the posterior instrumentation and a MED system or other MIS system could be used for the disc decompression and fusion with the IFR.

The paraspinal approach typically involves the following process.

Once the posterior elements are exposed, a typical laminotomy or facetectomy can be performed taking care not to damage the underlying dura or nervous tissues.

Retract the dura containing the cauda equine and the traversing nerve root to expose the posterior longitudinal ligament. Examine the canal for sequestered fragments and remove any tissue needed to decompress the cauda equine and nerve roots. Take care to release the nervous tissues and musculature at proper intervals to reestablish blood flow.

Incise the posterior annular wall and perform a complete nuclectomy taking care to leave the lateral and anterior annulus intact so that the annulus can be used to form a tension band in the fusion process. The endplates may then be prepared for fusion. In addition, lamina spreaders can be used if desired to make access for the nuclectomy easier. Bilateral access into the disc space for the nuclectomy can be used if desired with the paraspinal approach. Verify that the nuclectomy is complete by palpating the annular wall with an appropriate instrument (or alternatively by inflating a visualization balloon in the disc space and the using contrast medical and taking a suitable radiographic picture).

Next, the proper size IFR ring is chosen using any suitable method. Once a proper size is chosen, a balloon is placed into the interior cavity of the IFR and both are then collapsed and placed into the disc cavity using any suitable method for proper placement. Preferably, the IFR ring is inserted using minimally invasive techniques, such as by having the IFR ring and balloon folded so that it can be inserted using a small diameter catheter. Once inserted into the disc cavity, the balloon is filled with an incompressible fluid, such as contrast media, in order to deploy and unfold the IFR ring.

Once in place and unfolded, the next step is to prepare the PMMA bone cement and place the cement in any suitable injection device, such as a PMMA pump. The PMMA pump is connected to a polymer access port using a suitable delivery cannula. Using the PMMA pump, the IFR is filled to a recommended pressure and volume level for the IFR size chosen. The polymer delivery cannula is then removed and the material is allowed to cure. As described above, the polymer delivery cannula may be designed to allow for easy removal of the polymer delivery cannula from the injected PMMA, such as by rotating the cannula to "cut" the PMMA to separate the PMMA in the cannula from the PMMA injected inside the ring, so that the cannula is easily removed from the IBF ring While the PMMA material cures, it is possible to prepare a suitable fusion graft such as morselized bone graft material. Next, the vertebral endplates are prepared by exposing bleeding bone within the open, interior portion of the IFR. The interior portion of the IFR is filled with morselized bone graft material. As a final step, the access port is closed using any suitable method, such as by tying off the open access port of the IFR using nondegradable suture.

In addition, the surgical area may be irrigated as needed, and a standard closure technique performed to close the wound.

This invention is not to be taken as limited to all of the details thereof, as modifications and variations thereof may be made without departing from the spirit or scope of the invention.

The invention claimed is:

1. An orthopedic device for implanting between adjacent vertebrae comprising:

an injectable annular ring having inner and outer side walls defining an internal volume, the ring defining and bordering an interior cavity, the ring having upper and lower surfaces configured to engage adjacent vertebrae;

a web disposed within the internal volume of the ring, the web extending transversely through the internal volume of the ring parallel to and spaced from the upper and lower surfaces, the web connecting inner and outer side walls of the ring, the web structured to control cross-sectional expansion of the ring at forces within a range that will be applied to the device when engaging adjacent vertebrae of a patient;

at least one access port located on an exterior surface of an outer side wall of the ring open to the internal volume of the ring; and at least one access port located on an exterior surface of the ring open to the interior cavity bordered by the ring.

2. The device of claim 1 wherein the ring comprises a semi-permeable material porous to air and substantially non-porous to selected injectable fluids.

3. The device of claim 1 wherein the ring is a film, a knitted fabric, a woven fabric or a non-woven fabric.

4. The device of claim 3 wherein the fabric comprises threads or yarns.

5. The device of claim 2 wherein the ring is a fabric comprising a three-dimensional, non-orthogonal multifilament yarn structure.

6. The device of claim 5 wherein the three-dimensional structure comprises a honeycomb weave.

7. The device of claim 3 wherein the threads or yarns are comprised of fibers of polyacrylates, polyethylene, polypropylene, polyolefin copolymers, polycarbonates, polyesters, ether-ketone copolymers, polytetrafluoroethylene fibers, silk, polyurethanes, polyurethane co-polymers or mixtures thereof.

8. The device of claim 4 wherein at least a portion of the threads or yarns comprise consolidated, partially consolidated or heat set threads or yarns.

9. The device of claim 8 wherein the heat set threads or yarns provide a permanent shape memory to the fabric of the device.

10. The device of claim 4 wherein the threads or yarns comprise polyester fibers.

11. The device of claim 1 wherein the ring further comprises a flexible coating.

12. The device of claim 8 wherein the coating seals the ring.

13. The device of claim 8 wherein the coating promotes filling the internal volume of the ring with an injectable fluid.

14. The device of claim 8 wherein the coating comprises a thermal insulating material.

15. The device of claim 11 wherein the ring is coated with hydrogels, thermoset or thermoplastic urethanes, thermoset or thermoplastic elastomers, polytetrafluoroethylene fibers, polysiloxanes, polyvinylalcohols, proteins, collagen or mixture thereof.

16. The device of claim 15 wherein the ring is coated with a thermoplastic urethane.

17. The device of claim 1 wherein the web is a film, a knitted fabric, a woven fabric, a non-woven fabric, fibers, threads or yarns.

18. The device of claim 17 wherein the web is knitted or woven threads or yarns.

19. The device of claim 17 wherein the web is stitched threads or yarns.

20. The device of claim 17 wherein the web is stitched polyester threads.

21. The device of claim 1 wherein the web controls the cross-sectional expansion of the ring in a direction parallel to a horizontal mid-plane of the ring.

22. The device of claim 1 wherein cross-sectional expansion of the ring is greater in a direction perpendicular to a plane parallel to a horizontal mid-plane of the ring.

23. The device of claim 1 wherein the access ports are a single parallel port structure comprising at least one first aperture to the internal volume of the ring and at least one second aperture to the interior cavity bordered by the ring, wherein the first and second apertures are independent of each other.

24. The device of claim 1 wherein the access ports are a single coaxial port structure comprising at least one first aperture to the internal volume of the ring and at least one second aperture to the interior cavity bordered by the ring, wherein the first and second apertures are selectively independent of each other.

25. The device of claim 1 wherein the access ports are multiple structures comprising at least one first structure with an aperture to the internal volume of the ring and at least one second structure with an aperture to the interior cavity bordered by the ring.

26. The device of claim 1 further comprising a load-bearing, hardenable material.

27. The device of claim 26 wherein the load-bearing material comprises poly(lactic acid), poly(glycolic acid), p-dioxanone fibers, polyarylethyl, polyacrylates, polyurethanes, amino-acid-derived polycarbonates, polycaprolactones, aliphatic polyesters, calcium phosphate, unsaturated linear polyesters, vinyl pyrrolidones, polypropylene fumarate diacrylates, or mixtures thereof.

28. The device of claim 27 wherein the load-bearing material is polymethylmethacrylate.

29. The device of claim 27 wherein the load-bearing material is a bis-GMA polymer.

30. A spinal implant system for implantation between adjacent vertebrae comprising:
an injectable hollow annular ring including a web disposed within an internal volume of the ring, the web structured to control cross-sectional expansion of the ring at forces within a range that will be applied to the device when engaging adjacent vertebrae of a patient, wherein the web is attached to and extends between first and second opposing internal surfaces of the ring, the web extending parallel to and spaced apart from upper and lower walls of the ring, wherein the upper and lower walls are configured to engage adjacent vertebrae, at least one access port located on an exterior surface of the ring open to the internal volume of the ring, and at least one access port located on an exterior surface of the ring open to an interior cavity bordered by the ring;
a load-bearing material for injection in to the internal volume of the ring; and
an osteobiologic composition for placement in the interior cavity bordered by the ring.

31. The spinal implant system of claim 30 wherein the osteobiological composition comprises natural or synthetic graft substances promoting fusion of adjacent vertebrae.

32. The spinal implant system of claim 30 wherein the osteobiologic composition comprises mesenchymal stem cells, growth factors, cancellous bone chips, hydroxyapatite, tri-calcium phosphate, polylactic acid, polyglycolic acid, polygalactic acid, polycaprolactone, polyethylene oxide, polypropylene oxide, polysulfone, polyethylene, polypropylene, hyaluronic acid, bioglass, gelatin, collagen, polymeric fibers or mixtures thereof.

33. The spinal implant system of claim 30 further comprising a balloon sized and shaped to fit through the access port of the ring into the interior cavity bordered by the ring when collapsed and to expand in the interior cavity to distract adjacent vertebrae when filled with a fluid.

34. The spinal implant system of claim 30 further comprising at least one injection device to inject the load-bearing material into the internal volume of the ring, to expand a balloon sized and shaped to fit in the interior cavity bordered by the ring, or to inject the osteobiologic composition into the interior cavity bordered by the ring.

35. The spinal implant system of claim 30 further comprising at least one insertion device to place the ring in a collapsed state into an annular space between adjacent vertebrae.

36. The spinal implant system of claim 35 wherein the interior cavity of the ring contains a balloon that can be removed from the cavity through the access port.

37. A spinal implant kit for implantation between adjacent vertebrae comprising:
an injectable annular ring having upper and lower walls configured to engage adjacent vertebrae, the ring having a web disposed within an internal volume of the ring, the web extending transversely through the internal volume of the ring parallel to and spaced apart from upper and lower walls, connecting opposing side walls of the ring, the web structured to control cross-sectional expansion of the ring at forces within a range that will be applied to the device when engaging adjacent vertebrae of a patient, at least one access port disposed in a side wall of the ring, the access port open to the internal volume of the ring, and at least one access port open to an interior cavity bordered by the ring;

a load-bearing, hardenable material;
an osteobiologic composition;
a balloon sized and shaped to fit through the access port into the interior cavity bordered by the ring and to expand in the interior cavity to distract adjacent vertebrae;
at least one injection device to inject the load-bearing material into the internal volume of the ring, to fill the balloon, or to inject the osteobiologic composition into the interior cavity bordered by the ring; and
at least one insertion device to place the ring and balloon into a space between adjacent vertebrae.

* * * * *

UNITED STATES PATENT AND TRADEMARK OFFICE
CERTIFICATE OF CORRECTION

| | | |
|---|---|---|
| PATENT NO. | : 8,007,535 B2 | Page 1 of 1 |
| APPLICATION NO. | : 11/421571 | |
| DATED | : August 30, 2011 | |
| INVENTOR(S) | : Hudgins et al. | |

It is certified that error appears in the above-identified patent and that said Letters Patent is hereby corrected as shown below:

Column 1
Line 41, delete "Biedemmann", and insert therefor -- Biedermann --.

Signed and Sealed this
Twenty-second Day of November, 2011

David J. Kappos
*Director of the United States Patent and Trademark Office*